United States Patent [19]

Wadsworth, III et al.

[11] Patent Number: 4,909,264

[45] Date of Patent: Mar. 20, 1990

[54] PAD FOR ARTHOSCOPIC SURGERY STAND

[75] Inventors: Ralph A. Wadsworth, III, Whittier; Kerby L. Mellott, West Covina, both of Calif.

[73] Assignee: Convo Corporation, Chino, Calif.

[21] Appl. No.: 296,975

[22] Filed: Jan. 17, 1989

[51] Int. Cl.4 .............................................. A61F 3/00
[52] U.S. Cl. .................................... 128/845; 128/877; 128/878
[58] Field of Search ............... 128/877, 878, 879, 880, 128/881, 882; 269/322, 328; 5/481

[56] References Cited

U.S. PATENT DOCUMENTS

| 4,286,588 | 9/1981 | Lovegrove | 128/877 |
|---|---|---|---|
| 4,573,482 | 3/1986 | Williams, Jr. | 128/882 X |
| 4,730,610 | 3/1988 | Graebe | 128/882 |

Primary Examiner—Mickey Yu
Assistant Examiner—Lynda M. Cofsky
Attorney, Agent, or Firm—Harlan P. Huebner

[57] ABSTRACT

A foam pad for use with an arthoscopic surgery stand wherein said pad is adapted to wrap around the support element of the stand and be releasably retained thereon and a limb retaining means associated with the pad to secure on the pad and stand a limb of a person preparatory to surgery and recovery therefrom.

2 Claims, 2 Drawing Sheets

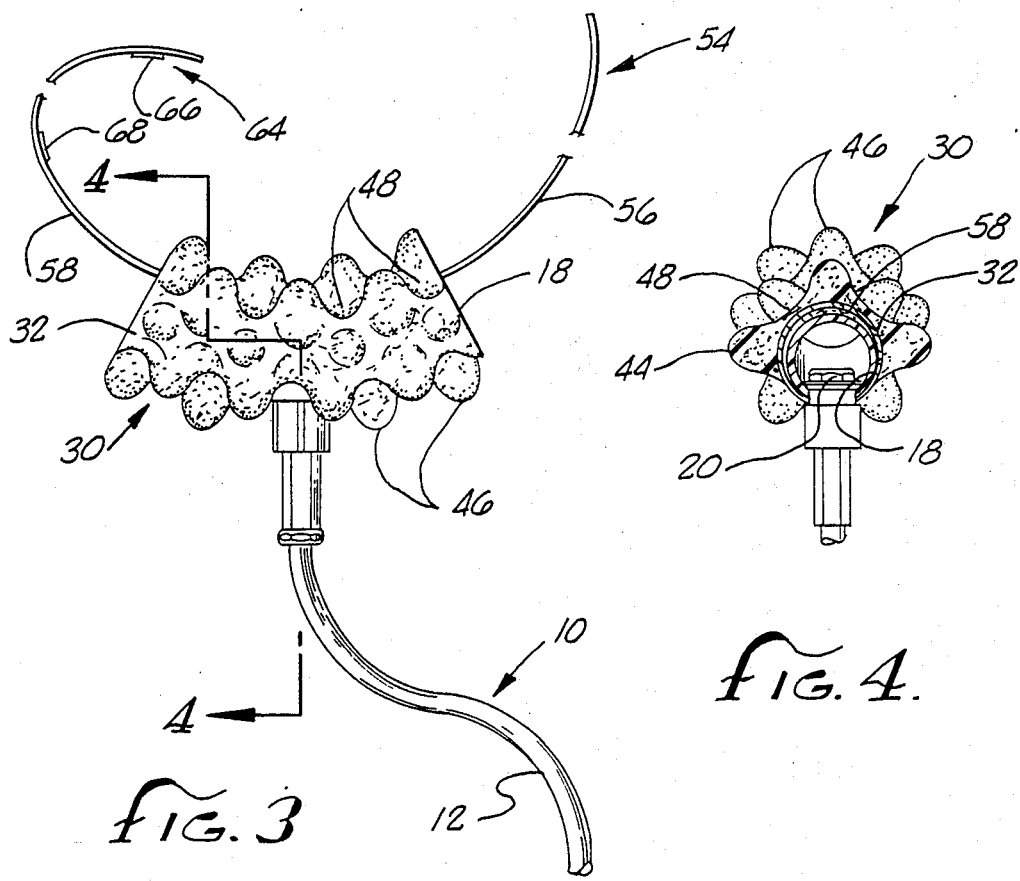
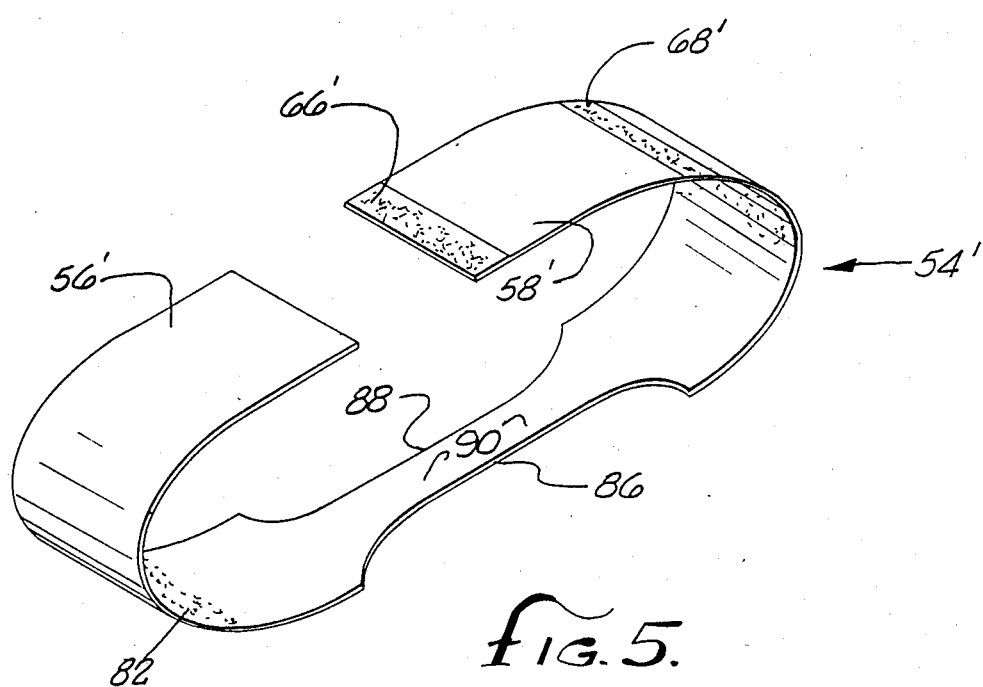

PAD FOR ARTHOSCOPIC SURGERY STAND

BACKGROUND OF THE INVENTION

1. Field of the Invention.

This invention relates to a pad and tie means for use with an arthoscopic surgery stand.

2. Description of the Prior Art.

With the development of arthoscopic surgery particularly in joints of humans, the need for hospital room surgery has to some extent been eliminated. In some cases the arthoscopic surgery may be performed in doctors offices without the need of hospital beds or operating tables.

The development of microsurgery on knees and elbows, known as arthoscopic surgery has resulted in the invention of an arthoscopic surgery stand to support the limb during surgery. Such a stand is the subject of a pending patent application and preferably includes a cradle member to receive the limb and the cradle is mounted on an adjustable stand which can be wheeled around an office or hospital for proper positioning.

With the advent of the arthoscopic surgery stand described above the present invention has come into being. Heretofore, there has been no prior art on the subject of cushioning pads for arthoscopic stands because no such stand had been developed.

SUMMARY OF THE INVENTION

It is the purpose of the present invention to provide a foam limb cushioning pad for use with an arthoscopic surgery stand.

Another object of the present invention is to provide a foam limb cushioning pad that is removable from a support stand so that the same may be sterilized or replaced with a new pad.

A further object is to provide a foam limb cushioning pad that has associated with it strap means to retain the human limb in position on the stand.

A still further object of the present invention is to provide a pad of convoluted foam whereby the limb resting thereon may be elevated above the stand and air allowed to circulate around the limb in the area of contact with the pad.

Another object of the present invention is to provide a foam limb cushioning pad wherein the strap means are secured together to hold the limb.

A still further object of the present invention is to provide an open cell polyurethane foam pad adapted to cushion a limb from a stand during arthoscopic surgery and post surgery rest.

These and other objects and advantages will become apparent from the following part of the specification wherein details have been described for the competence of disclosure, without intending to limit the scope of the invention which is setforth in the appended claims.

BRIEF DESCRIPTION OF THE DRAWINGS

These advantages may be more clearly understood from the following detailed description and by reference to the drawings in which:

FIG. 3 is a side elevational view of the pad of the present invention on an arthoscopic surgery stand;

FIG. 4 is a cross sectional view taken on line 4—4 of FIG. 3; and

FIG. 5 is a perspective view of a modified strap of the present invention that is separate but associated with the pad of the present invention.

DETAILED DESCRIPTION OF THE PREFERRED EMBODIMENT

Figure 1:
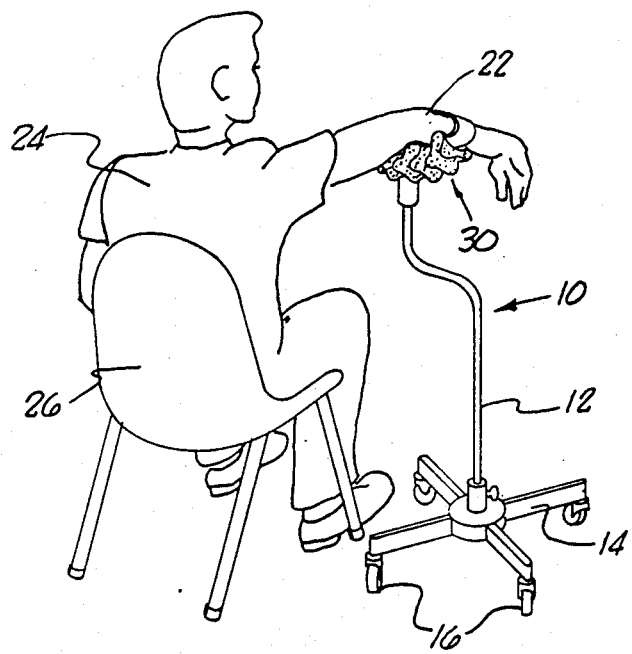
FIG. 1 is an environmental view of an arthoscopic surgery stand and the pad of the present invention in place supporting the elbow of a patient.

Referring to the drawings in FIGS. 1 and 3 there is illustrated a stand 10 generally designated for performing arthoscopic surgery. The stand 10, for background and not forming a part of the present invention, preferably includes an adjustable vertical rod 12 which may be seated in a caster assembly 14 having casters or wheels 16 to move the stand 10 around.

Mounted on top of the adjustable rod 12 is a tubular member 18. The member 18 is mounted on the rod 12 by a nut and bolt means 20. The tubular support member 18 may be of plastic and is dished so as to cradle a limb or elbow 22 of a patient 24. As can be seen the patient 24 may be seated in chair 26 and the rod 12 adjusted to present the elbow 22 to the doctor for the surgery. On the other hand if a knee is involved then the patient 24 may lay on a bed with the leg extending over the edge of the bed resting on the stand 10.

Figure 2:
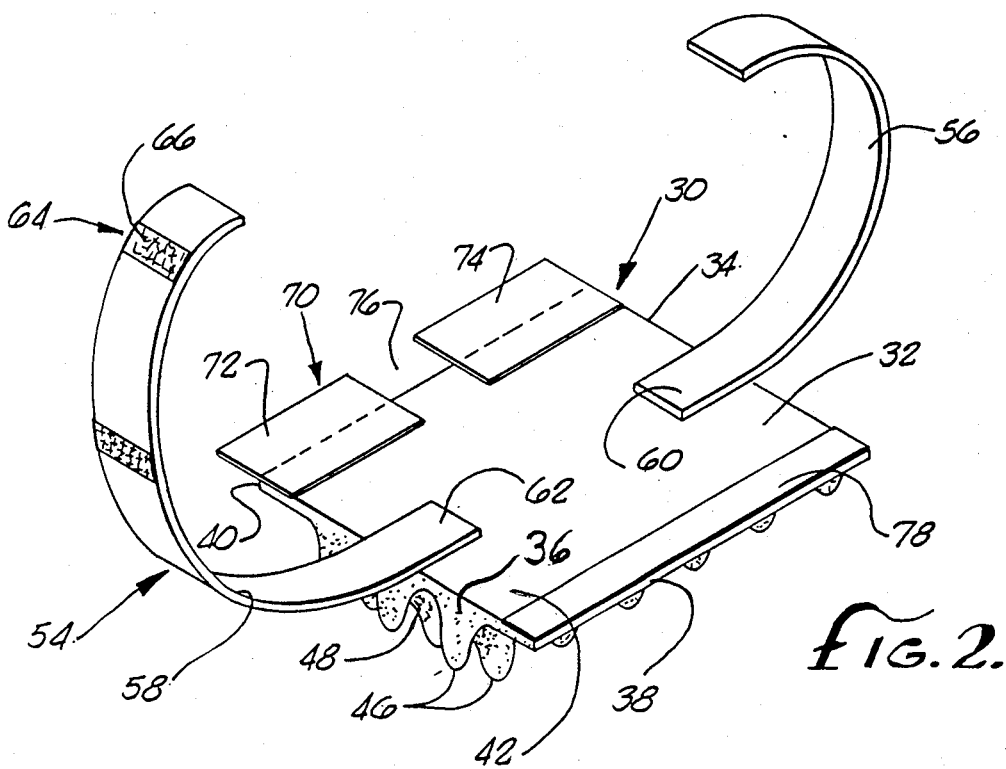
FIG. 2 is a prospective view of the pad of the present invention with a strap attached thereto.

The present invention for use with the stand 10 includes a pad generally designated 30, best illustrated in FIG. 2. The pad 30 is adapted to be wrapped around the tubular support member 18 and secured therearound to be described in more detail.

The pad 30 is preferably made of open cell polyurethane foam and is a sheet 32 of preferably rectangular shape having opposed parallel edges 34 and 36 which are normal to edges 38 and 40.

The bottom surface 42 of the pad 30 is generally flat or uninterrupted and the top or upper surface 44 is convoluted, as best seen in FIGS. 1, 3 and 4. The convolutions of open cell foam is well known in the trade and there is commercial equipment available to roll foam therethrough and create spaced apart peaks 46 with valleys 48 therebetween.

While the foam outer or top surface 44 is preferred convoluted, a flat top surface may also be used to accomplish the intended result. The main concern is to cushion the limb in the area of the elbow 22, as an illustration, to assure as much comfort as possible during the arthoscopic surgery.

The pad 30 is also fitted with limb retaining means generally designated 54 for the purpose of holding a patient's limb fixed on the surgery stand 10 during an operation. The limb retaining means 54 as shown in FIG. 2 may include a two piece strap with sections 56 and 58 of flexible material such as cotton. The retaining means 54 may also be a one piece structure, secured to the pad 30 without departing from the spirit of the invention.

Each end 60 and 62 of the respective straps 56 and 58 are secured by adhesive or other conventional means to the bottom surface 42 of the rectangular sheet 32. The straps 56 and 58 are elongated and project normal to the edges 34 and 36 of the sheet 32. They are of a combined length to reach around the limb of the patient 24 and be adjustably secured together.

Preferably the strap sections 56 and 58 include hook and loop fastening means generally designated 64 of hook and/or loop strips 66 and 68 which are sold under the trademark Velcro and are representative of the fasteners which may be used. Once the limb is placed on the pad the two straps 56 and 58 are pulled around the limb and at least one of the straps is pressed into the material straps to fasten the straps about the limb.

In order to releasably maintain the pad 30 on the tubular support member 18, the pad retaining means 70 includes hook and/or loop tabs 72 and 74 which are secured to the bottom 42 of the pad by any conventional means and project outward of edge 40. The tabs 72 and 74, as best seen in FIG. 2, are spaced apart forming an opening 76 therebetween. The purpose of the opening 76 is to receive the rod 12 as the pad 30 is wrapped around the tubular support member 18 and allow the pad 30 to be retained in a relatively smooth uninterrupted position around the member 18.

At the opposed edge 38 a strip of soft hook and/or loop material 78 is applied to the pad 30. The purpose of the material is to catch and releasably hold the strips or tabs 72 and 74 when the pieces are engaged together.

While it is preferable to have the limb retaining means 54 integral with the pad 30 a retaining means 54′ as illustrated in FIG. 5 may be used. The means 54′ is associated with the pad 30 by being a single piece of flexible material 82 that passes through the tubular support member 18 and around the limb. There are the hook and loop strips 66′ and 68′ that were previously described to attach the overlapped other end of the strap sections 56′ and 58′.

In order to prevent the retaining means 54′ from buckling and not lying flat as it passes through the tubular member 18 the width of the strap may be thinned by cutting opposed recesses 86 and 88 so as to have a center section 90 of a width less than the interior diameter of the tubular member 18.

The invention and its attendant advantages will be understood from the foregoing description and it will be apparent that various changes may be made in the form, construction and arrangements of the parts without departing from the spirit and scope thereof or sacrificing its material advantages, the arrangements herein before described being merely by way of example. I do not wish to be restricted to the specific forms shown or uses mentioned, except as defined in the accompanying claims, wherein various portions have been separated for clarity of reading and not for emphasis.

We claim:

1. A foam pad for use with an arthoscopic surgery stand wherein the stand includes and elongated tubular limb supporting cradle member to receive the limb of a person and said member is mounted on a vertical cradle support shaft, said foam pad comprising:

a generally rectangular non-limb encasing from sheet including a bottom and a top surface and first and second pairs of opposed generally parallel edges defining the perimeter of said foam sheet adapted to encase said cradle member with said bottom surface and cushion a limb which is placed on said top surface;

pad retaining means on each of the edges of one of the pairs of opposed generally parallel edges adapted to engage each other to fasten said foam sheet around said tubular limb supporting cradle, said pad retaining means include hook and loop strips projecting from one edge and strip engaging material on the opposed edge capable of being releasably maintained to said strips when in contact therewith; and limb retaining means associated with said generally rectangular foam sheet projecting from said other of said pairs of opposed generally parallel edges adapted to pass around a limb resting on said foam sheet pad and engage each other to releasably lock said limb on said pad.

2. A foam pad as defined in claim 1 wherein said generally rectangular foam sheet includes;

convolutions of foam forming said top surface, said convolutions being a plurality of spaced apart peaks broken by a plurality of valleys between said peaks.

* * * * *